United States Patent
Seong

(10) Patent No.: US 10,397,456 B2
(45) Date of Patent: Aug. 27, 2019

(54) APPARATUS FOR INSPECTING EDGE OF SUBSTRATE

(71) Applicant: Corning Precision Materials Co., Ltd., Chungcheongnam-do (KR)

(72) Inventor: Siho Seong, Chungcheongnam-do (KR)

(73) Assignee: Corning Precision Materials Co., Ltd. (KR)

( * ) Notice: Subject to any disclaimer, the term of this patent is extended or adjusted under 35 U.S.C. 154(b) by 878 days.

(21) Appl. No.: 14/596,650

(22) Filed: Jan. 14, 2015

(65) Prior Publication Data

US 2015/0198539 A1    Jul. 16, 2015

(30) Foreign Application Priority Data

Jan. 15, 2014  (KR) .................. 10-2014-0004875

(51) Int. Cl.

| | | |
|---|---|---|
| *G01N 21/95* | (2006.01) | |
| *H04N 5/225* | (2006.01) | |
| *G01N 21/958* | (2006.01) | |
| *H01L 21/67* | (2006.01) | |
| *G01N 21/896* | (2006.01) | |

(52) U.S. Cl.
CPC ......... *H04N 5/2256* (2013.01); *G01N 21/896* (2013.01); *G01N 21/958* (2013.01); *H01L 21/67288* (2013.01); *G01N 21/9503* (2013.01); *G01N 2201/062* (2013.01); *G01N 2201/105* (2013.01)

(58) Field of Classification Search
CPC ......... G01N 21/9503; G01N 2201/062; G01N 2201/105; G01N 21/958; G01N 21/896; H04N 5/2256; H01L 21/67288
See application file for complete search history.

(56) References Cited

U.S. PATENT DOCUMENTS

| | | | | |
|---|---|---|---|---|
| 5,260,558 A | * | 11/1993 | Goltsos | G01B 11/02 250/205 |
| 5,298,939 A | * | 3/1994 | Swanson | G03F 7/70275 355/30 |
| 6,434,087 B1 | * | 8/2002 | Schell | G11B 11/10506 369/116 |
| 6,449,103 B1 | * | 9/2002 | Charles | G02B 13/06 359/366 |
| 6,618,209 B2 | * | 9/2003 | Nishioka | G02B 1/06 359/291 |

(Continued)

Primary Examiner — Sathyanaraya V Perungavoor
Assistant Examiner — Philip P. Dang
(74) Attorney, Agent, or Firm — Lerner, David, Littenberg, Krumholz & Mentlik, LLP

(57) ABSTRACT

An apparatus for inspecting an edge portion of a substrate can inspect a defect or a chamfered width on an edge portion of a substrate. First and second right-angled prisms are disposed above and below the edge portion such that inclined surfaces thereof are directed toward the upper surface and lower surface of the edge portion. A lighting part irradiates the edge portion of the substrate with light. A photographing part is disposed adjacent to the edge portion. The photographing part takes an image of the upper surface of the edge portion from light that has passed through the first right-angled prism, an image of the lower surface of the edge portion from light that has passed through the second right-angled prism, and an image of an end surface of the edge portion.

7 Claims, 3 Drawing Sheets

(56) References Cited

U.S. PATENT DOCUMENTS

| | | | | |
|---|---|---|---|---|
| 7,054,075 B2* | 5/2006 | Nishioka | .................. | G02B 1/06 |
| | | | | 359/290 |
| 7,130,136 B2* | 10/2006 | Fujimori | .............. | H04N 9/3141 |
| | | | | 359/820 |
| 7,400,439 B2* | 7/2008 | Holman | .................... | F21S 8/08 |
| | | | | 359/298 |
| 7,436,486 B2* | 10/2008 | Hirukawa | ........... | G03F 7/70341 |
| | | | | 355/53 |
| 7,795,886 B2* | 9/2010 | Kono | .................... | G01R 29/12 |
| | | | | 324/754.22 |
| 7,960,750 B2* | 6/2011 | Kim | ........................ | H01L 33/60 |
| | | | | 257/98 |
| 2004/0080938 A1* | 4/2004 | Holman | .................... | F21S 8/08 |
| | | | | 362/231 |
| 2007/0177138 A1* | 8/2007 | Esmaeili | ............ | G01N 21/8806 |
| | | | | 356/241.1 |
| 2010/0202048 A1* | 8/2010 | Amitai | ................. | H04N 13/344 |
| | | | | 359/485.02 |
| 2011/0157097 A1* | 6/2011 | Hamada | .............. | G02F 1/13338 |
| | | | | 345/175 |
| 2012/0140146 A1* | 6/2012 | Baba | ................. | G02F 1/133603 |
| | | | | 349/62 |
| 2012/0287674 A1* | 11/2012 | Nichol | ................. | G02B 6/0018 |
| | | | | 362/611 |
| 2013/0085328 A1* | 4/2013 | Kitano | ............... | A61B 1/00096 |
| | | | | 600/110 |
| 2013/0208198 A1* | 8/2013 | Choi | ................. | G02F 1/133382 |
| | | | | 349/15 |

* cited by examiner

APPARATUS FOR INSPECTING EDGE OF SUBSTRATE

BACKGROUND OF THE INVENTION

Field of the Invention

The present invention relates to an apparatus for inspecting an edge portion of a substrate, and more particularly, to an apparatus for inspecting an edge portion of a substrate able to inspect a defect or a chamfered width on an edge portion of a substrate.

Description of Related Art

A glass substrate used in flat panel displays, such as thin-film transistor liquid crystal displays (TFT-LCDs), plasma display panels (PDPs) and electroluminescent (EL) displays, is manufactured by a shaping process of shaping molten glass produced from a glass melting furnace into a flat glass plate and a cutting process of cutting the flat glass plate according to predetermined dimensions. The manufactured glass substrate is subsequently transported to a machining line, in which the glass substrate is in turn machined. In the machining line, the glass substrate is cut again according to the dimension of a flat panel display in which the glass substrate is to be used, and subsequently the four edges of the glass substrate are chamfered. The chamfering process is intended to prevent the four edge portions of the glass substrate from being easily damaged by, for example, external impacts by making the edge portions round. When the chamfering process is carried out, as shown in FIG. 1, the edge portions of the substrate generally has the upper surface, the end surface and the lower surface. Although the chamfered upper and lower surfaces of the edge portion of the substrate are required to be symmetrical to each other, the upper and lower surfaces are, in fact, asymmetrical.

After the chamfering process, an inspection process is carried out to inspect whether or not a defect, such as a crack, has occurred on the edge portion chamfered at the chamfering process and to inspect the width of the chamfered portion.

In the related art, this inspection process is carried out by an inspection apparatus disclosed in Patent Document 1.

However, the inspection apparatus disclosed in Patent Document 1 has a drawback in that this apparatus must use a plurality of optical devices in order to inspect the upper surface, the lower surface and the end surface of the edge portion, respectively.

The inspection apparatus disclosed in the Patent Document has another drawback in that it is difficult to precisely measure the width of the chamfered portion since coaxial illumination is used. This is because the upper surface and the lower surface of the edge portion are inspected on the same line and thus the surface that is being inspected is influenced by an afterimage of a chamfering reference line occurring on the opposite side.

The information disclosed in the Background of the Invention section is provided only for better understanding of the background of the invention and should not be taken as an acknowledgment or any form of suggestion that this information forms a prior art that would already be known to a person skilled in the art.

RELATED ART DOCUMENT

Patent Document 1: Korean Patent No. 10-0579322 (May 4, 2006)

BRIEF SUMMARY OF THE INVENTION

Various aspects of the present invention provide an apparatus for inspecting an edge portion of a substrate able to inspect a defect on an edge portion of a substrate using a simpler structure. In addition, also provided is an apparatus for inspecting an edge portion of a substrate able to more precisely measure a chamfered width on an edge portion of a substrate.

In an aspect of the present invention, provided is an apparatus for inspecting an edge portion of a substrate including: a first right-angled prism disposed above an edge portion of a substrate such that an inclined surface thereof is directed toward the upper surface of the edge portion of the substrate; a second right-angled prism disposed below the edge portion of the substrate such that an inclined surface thereof is directed toward the lower surface of the edge portion of the substrate; a lighting part irradiating the edge portion of the substrate with light; and a photographing part disposed adjacent to the edge portion of the substrate. The photographing part takes an image of the upper surface of the edge portion of the substrate from light that has passed through the first right-angled prism, an image of the lower surface of the edge portion of the substrate from light that has passed through the second right-angled prism, and an image of the end surface of the edge portion of the substrate.

The apparatus may further include: a first correction plate disposed between the first right-angled prism and the photographing part to reduce a path of light that has passed through the first right-angled prism; and a second correction plate disposed between the second right-angled prism and the photographing part to reduce a path of light that has passed through the second right-angled prism. Here, the first correction plate and the second correction plate may be formed of BK7.

An angle between an upper surface and the inclined surface of the first right-angled prism and an angle between a lower surface and the inclined surface of the second right-angled prism may be an acute angle smaller than 45°.

The apparatus may further include a display part displaying the images taken by the photographing part.

The apparatus may further include an air nozzle removing impurities from the edge portion of the substrate by ejecting air onto the edge portion of the substrate.

The apparatus may further include a transportation part transporting the substrate.

According to the present invention, it is possible to obtain images from all of the upper surface, the lower surface and the end surface of an edge portion of a substrate using a single optical device.

In addition, according to the present invention, the images of the upper surface and the lower surface of the edge portion of the substrate are obtained from light incident onto the inclined surfaces of the right-angled prisms that are directed a predetermined angle with respect to the upper and lower surface of the edge portion of the substrate without the use of coaxial illumination. This can consequently prevent each surface to be inspected from being influenced by an afterimage of a chamfering reference line occurring on the opposite surface, whereby the chamfered width can be precisely measured.

The methods and apparatuses of the present invention have other features and advantages that will be apparent from or are set forth in greater detail in the accompanying drawings which are incorporated herein, and in the following Detailed Description of the Invention, which together serve to explain certain principles of the present invention.

DETAILED DESCRIPTION OF THE INVENTION

Figure 1:
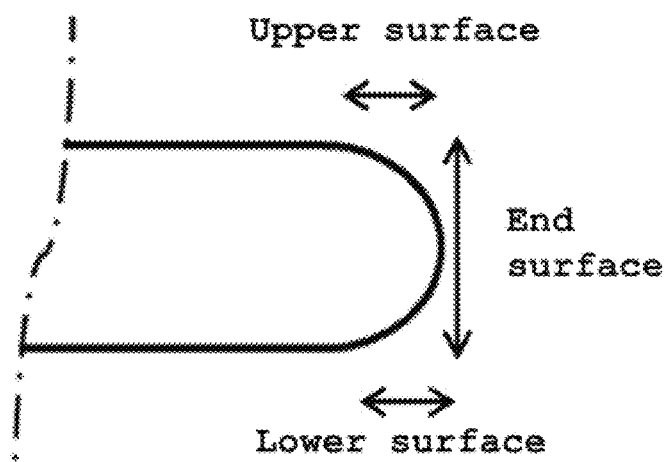
FIG. 1 is a conceptual view illustrating a chamfered edge portion of a substrate.

Reference will now be made in detail to exemplary embodiments of an apparatus for inspecting an edge portion of a substrate according to the present invention in conjunction with the accompanying drawings so that a person skilled in the art to which the present invention relates could easily put the present invention into practice.

Throughout this document, reference should be made to the drawings, in which the same reference numerals and symbols are used throughout the different drawings to designate the same or similar components. In the following description of the present invention, detailed descriptions of known functions and components incorporated herein will be omitted in the case that the subject matter of the present invention is rendered unclear.

Figure 2:
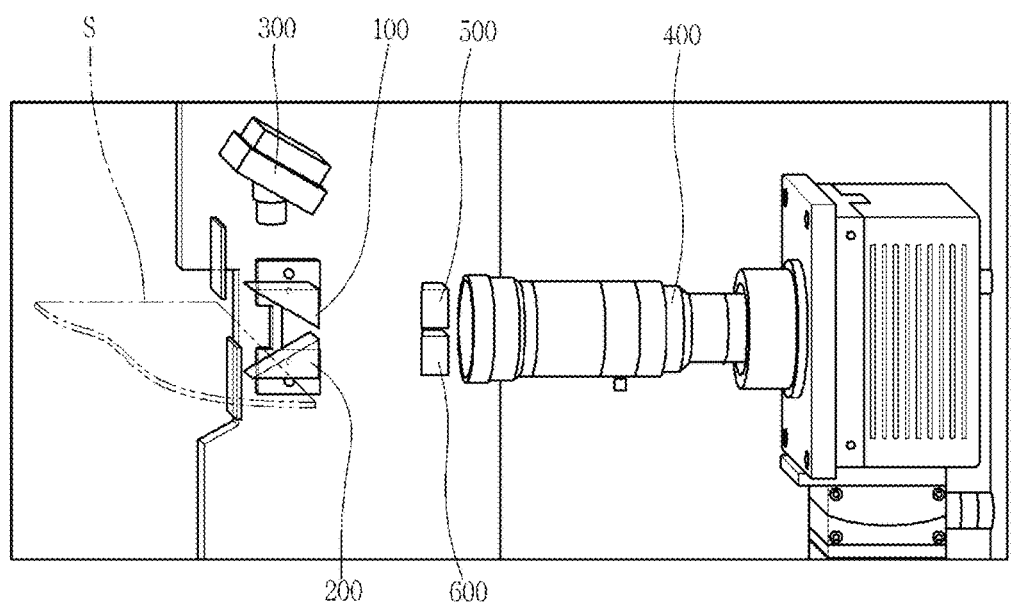
FIG. 2 is a schematic configuration view illustrating an apparatus for inspecting an edge portion of a substrate according to an exemplary embodiment of the present invention.

FIG. 2 is a schematic configuration view illustrating an apparatus for inspecting an edge portion of a substrate according to an exemplary embodiment of the present invention.

The apparatus for inspecting an edge portion of a substrate (hereinafter referred to as the "substrate edge inspection apparatus") according to an exemplary embodiment of the present invention is an apparatus for inspecting a defect or a chamfered width present on a chamfered edge portion of a substrate S, more particularly, a glass substrate used in a flat panel display, such as a thin-film transistor liquid crystal display (TFT-LCD) or an organic light-emitting diode (OLED) display. As illustrated in FIG. 2, the substrate edge inspection apparatus includes a first right-angled prism 100, a second right-angled prism 200, a lighting part 300 and a photographing part 400.

The first right-angled prism 100 is disposed above the edge portion of the substrate S to be inspected such that an inclined surface thereof is directed toward the upper surface of the edge portion of the substrate S to be inspected.

The second right-angled prism 200 is disposed below the edge portion of the substrate S to be inspected such that an inclined surface thereof is directed toward the lower surface of the edge portion of the substrate S to be inspected.

The first right-angled prism 100 positioned above the edge portion of the substrate S to be inspected is spaced apart a predetermined distance from the second right-angled prism 200 positioned below the edge portion of the substrate S to be inspected. The distance is to be greater than the thickness of the substrate S.

It is preferable that the first right-angled prism 100 and the second right-angled prism 200 are positioned such that they face each other.

The upper surface of the first right-angled prism 100 and the lower surface of the second right-angled prism 200 may be parallel with the upper/lower surface of the substrate S.

It is preferable that the first right-angled prism 100 and the second right-angled prism 200 are symmetric with respect to a line (surface) longitudinally extended from the substrate S.

Figure 3:
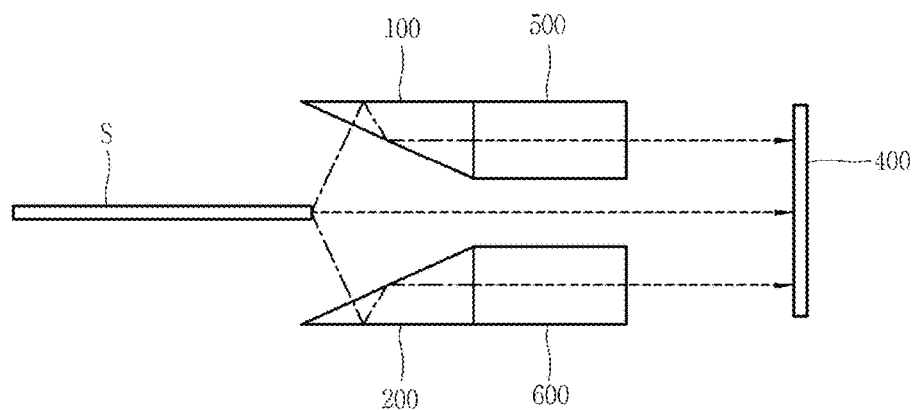
FIG. 3 is a conceptual diagram illustrating the process of taking images from the upper surface, the lower surface and the end surface of an edge portion of a substrate using the apparatus for inspecting an edge portion of a substrate according to an exemplary embodiment of the present invention.

The first right-angled prism 100 and the second right-angled prism 200 allow the photographing part 400 to take images from the upper and lower surfaces of the edge portion of the substrate S through optical paths, as illustrated in FIG. 3.

It is preferable that an angle between an upper surface and the inclined surface of the first right-angled prism 100 and an angle between a lower surface and the inclined surface of the second right-angled prism 200 are an acute angle smaller than 45°.

The smaller the acute angle is, the smaller the distances between the upper surface, the lower surface and the end surface of the edge portion of the substrate S obtained by the photographing part 400 will be. Accordingly, it is possible to obtain high-resolution images from the upper, lower and end surfaces.

The lighting part 300 irradiates the edge portion of the substrate S with light.

The lighting part 300 may radiate light from a light-emitting diode (LED) light source, and may be disposed at a plurality of positions in order to obtain clearer images.

The photographing part 400 is disposed adjacent to the edge portion of the substrate S, and takes an image of the upper surface of the edge portion of the substrate S from light that has passed through the first right-angled prism 100, an image of the lower surface of the edge portion of the substrate S from light that has passed through the second right-angled prism 200, and an image of the end surface of the edge portion of the substrate S.

That is, the photographing part 400 takes the image of the upper surface and the image of the lower surface of the edge portion of the substrate S from light that has passed through the first right-angled prism 100 and the second right-angled prism 200, respectively. The photographing part 400 also takes the image of the end surface from light that is directly incident thereon through the space between the first right-angled prism 100 and the second right-angled prism 200. For this, it is preferable that the photographing part 400 is disposed at a position facing the edge portion of the substrate S.

It is preferable that a line longitudinally extended from the substrate S passes through the center of the photographing part 400.

The photographing part 400 may include a lens and a camera. The camera may be implemented as a line scan camera.

Since the substrate edge inspection apparatus according to the present invention is configured as above, it is possible to inspect the upper surface, the lower surface and the end surface of the chamfered edge portion of the substrate using a single optical device.

In addition, the substrate edge inspection apparatus according to the present invention obtains images from the upper surface and the lower surface of the edge portion of the substrate using light incident onto the inclined surfaces of the first right-angled prism 100 and the second right-angled prism 200 that are directed a predetermined angle with respect to the upper and lower surfaces of the edge portion of the substrate, respectively, without the use of coaxial illumination. This can consequently prevent each surface to be inspected from being influenced by an afterimage of a chamfering reference line occurring on the opposite surface, whereby the chamfered width can be precisely measured. Since the upper surface and the lower surface of the edge portion of the substrate are inspected in the state in which they are inclined at the predetermined angle, an error may occur in the measurement of the chamfered width of either the upper surface or the lower surface of the edge portion of the substrate. However, this error can be corrected. Specifically, an actual chamfered width may be calculated from the measurement having the error by compensating for a value corresponding to the angle.

Figure 4:
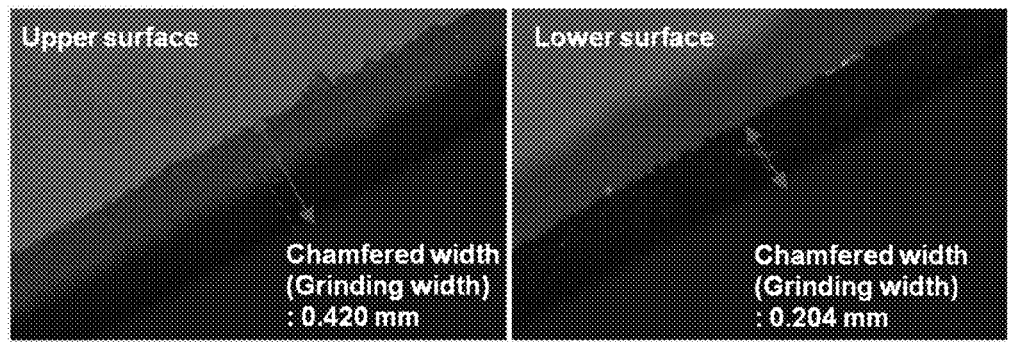
FIG. 4 illustrates pictures of the upper surface and the lower surface of a chamfered edge portion of a substrate taken using a microscope under coaxial illumination.

FIG. 4 illustrates pictures of the upper surface and the lower surface of a chamfered edge portion of a substrate taken using a microscope under coaxial illumination. As illustrated in FIG. 4, the image of either the upper surface or the lower surface of the edge portion of the substrate taken using microscope under coaxial illumination contains a chamfering reference line of the opposite surface. This may cause an error in the calculation of a chamfered width.

Figure 5:
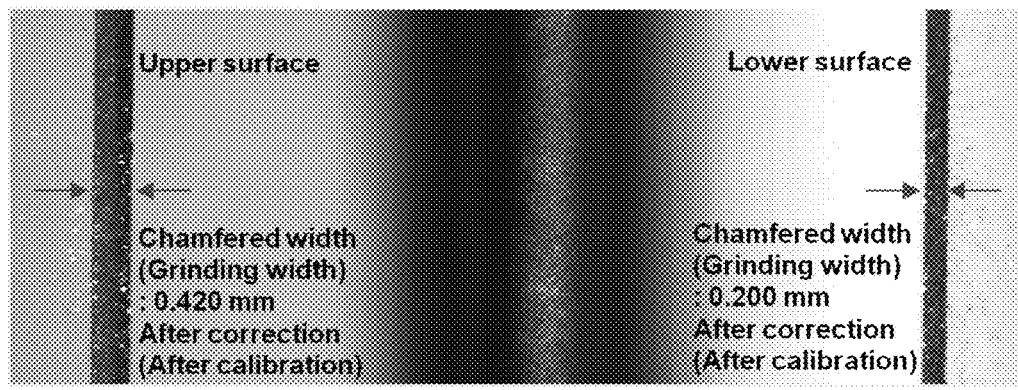
FIG. 5 illustrates pictures of the upper surface and the lower surface of a chamfered edge portion of a substrate taken from using the apparatus for inspecting an edge portion of a substrate according to an exemplary embodiment of the present invention.

FIG. 5 illustrates pictures of the upper surface and the lower surface of a chamfered edge portion of a substrate taken from using the substrate edge inspection apparatus according to an exemplary embodiment of the present invention. As illustrated in FIG. 5, the image taken from either the upper or lower surface of the chamfered substrate using the substrate edge inspection apparatus according to an exemplary embodiment of the present invention does not contain a chamfering reference line of the opposite surface. Consequently, no error occurs in the calculation of a chamfered width, and a calculated value of the chamfered width can be equal to or very close to an actual value of the chamfered width.

Figure 6:
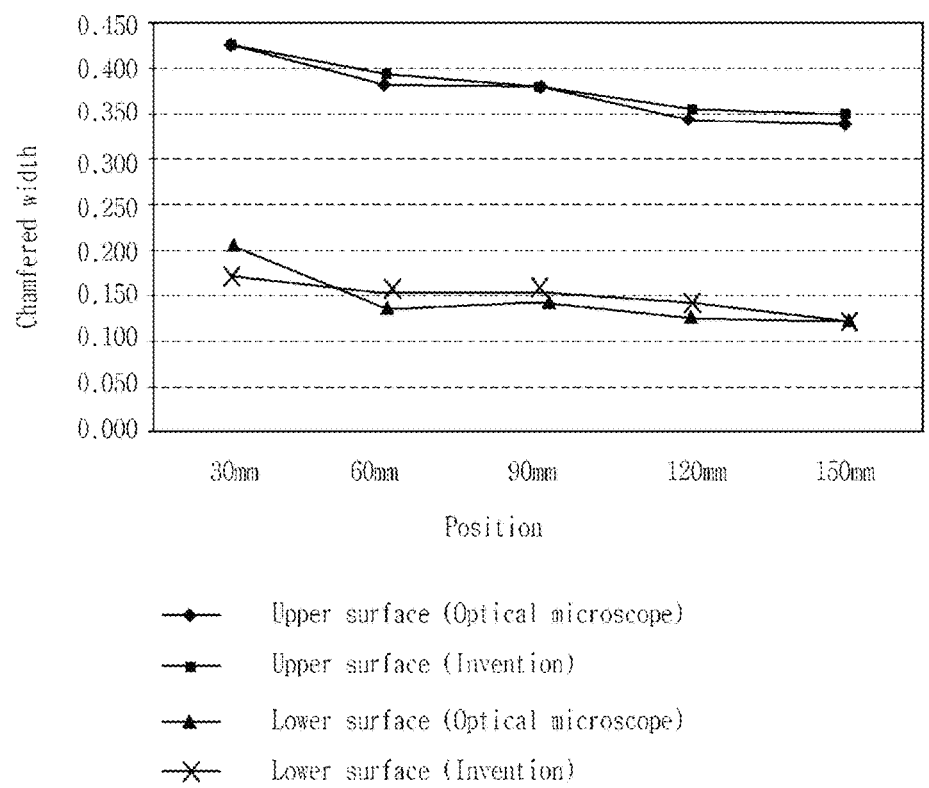
FIG. 6 illustrates a graph of the chamfered widths of a glass substrate according to positions measured using the apparatus for inspecting an edge portion of a substrate according to an exemplary embodiment of the present invention and an optical microscope.

FIG. 6 illustrates a graph of the chamfered widths of a glass substrate according to positions measured using the substrate edge inspection apparatus according to an exemplary embodiment of the present invention and an optical microscope.

As illustrated in FIG. 6, it is appreciated that the chamfered widths measured using the optical microscope are substantially the same as the chamfered widths measured using the substrate edge inspection apparatus according to an exemplary embodiment of the present invention.

Returning to FIG. 2, the substrate edge inspection apparatus according to an exemplary embodiment of the present invention further includes a first correction plate 500 and a second correction plate 600. The first correction plate 500 is disposed between the first right-angled prism 100 and the photographing part 400 to reduce the path of light that has passed through the first right-angled prism 100. The second correction plate 600 is disposed between the second right-angled prism 200 and the photographing part 400 to reduce the path of light that has passed through the second right-angled prism 200.

As illustrated in FIG. 3, the image of either the upper or lower surface of the edge portion of the substrate S is obtained from light that has passed through either the first right-angled prism 100 or the second right-angled prism 200, whereas the image of the end surface of the edge portion of the substrate S is directly obtained from the end surface of the edge portion of the substrate S. Therefore, the path of light entering the photographing part 400 through either the first right-angled prism 100 or the second right-angled prism 200 from either the upper or lower surface of the edge portion of the substrate S is longer than the path of light entering the photographing part 400 from the end surface of the edge portion of the substrate S. This may consequently cause a problem of focus mismatch in the photographing part 400.

In order to overcome this problem, according to an exemplary embodiment of the present invention, the first correction plate 500 and the second correction plate 600 are respectively disposed between the first right-angled prism 100 and the photographing part 400 and between the second right-angled prism 200 and the photographing part 400. This consequently reduces the paths of light entering the photographing part 400 from the first right-angled prism 100 and the second right-angled prism 200, thereby matching the focuses of the upper surface, the lower surface and the end surface of the edge portion of the substrate S taken by the photographing part 400. Specifically, it is possible to match the focuses of the upper surface, the lower surface and the end surface of the edge portion of the substrate S taken by the photographing part 400 by adjusting the material, thickness and length of either the first correction plate 500 or the second correction plate 600 such that the length of the path of light entering the photographing part 400 through the first right-angled prism 100 and the first correction plate 500 from the upper surface of the edge portion of the substrate S, the length of the path of light entering the photographing part 400 through the second right-angled prism 200 and the second correction plate 600 from the lower surface of the edge portion of the substrate S, and the length of the path of light entering the photographing part 400 from the end surface of the edge portion of the substrate S are the same.

It is preferable that the first correction plate 500 and the second correction plate 600 are formed of BK7 (borosilicate crown glass).

The thickness and length of either the first correction plate 500 or the second correction plate 600 may be suitably controlled according to predetermined conditions, such as the angle between the substrate and the right-angled prism and the length between the right-angled prism and the photographing part.

In addition, the substrate edge inspection apparatus according to an exemplary embodiment of the present invention further includes a display part (not shown) for displaying images taken by the photographing part 400.

The display part (not shown) may calculate a defect or a chamfered width on the chamfered edge portion by processing the images taken by the photographing part 400, and display the result of the calculation on a display device.

In addition, the substrate edge inspection apparatus according to an exemplary embodiment of the present invention further includes an air nozzle (not shown) that removes impurities from the edge portion of the substrate by ejecting air onto the edge portion.

The air nozzle (not shown) removes impurities from the edge portion of the substrate by ejecting air supplied from an air source (not shown) onto the edge portion of the substrate, thereby preventing impurities from appearing on an image taken from any one of the upper, lower and end surfaces of the edge portion of the substrate taken by the photographing part 400.

Furthermore, the substrate edge inspection apparatus according to an exemplary embodiment of the present invention further includes a substrate transportation part (not shown) that transports the substrate.

As set forth above, the substrate edge inspection apparatus, i.e. the apparatus for inspecting an edge portion of a substrate, according to the present invention can continuously inspect the edge portion of the substrate transported by the substrate transportation part (not shown), thereby improving the efficiency of the inspection on the edge portion of the substrate.

The foregoing descriptions of specific exemplary embodiments of the present invention have been presented with respect to the drawings. They are not intended to be exhaustive or to limit the present invention to the precise forms disclosed, and obviously many modifications and variations are possible for a person having ordinary skill in the art in light of the above teachings.

It is intended therefore that the scope of the present invention not be limited to the foregoing embodiments, but be defined by the Claims appended hereto and their equivalents.

What is claimed is:

1. An apparatus for inspecting an edge portion of a substrate, comprising:
    a first right-angled prism disposed above an edge portion of a substrate such that an inclined surface thereof is directed toward an upper surface of the edge portion of the substrate;
    a second right-angled prism disposed below the edge portion of the substrate such that an inclined surface thereof is directed toward a lower surface of the edge portion of the substrate;
    a lighting part directly irradiating the edge portion of the substrate with light; and
    a photographing part disposed adjacent to the edge portion of the substrate, wherein the photographing part takes an image of the upper surface of the edge portion of the substrate from light that has passed through the first right-angled prism, an image of the lower surface of the edge portion of the substrate from light that has passed through the second right-angled prism, and an image of an end surface of the edge portion of the substrate;
    wherein the lighting part is disposed on a side of the edge portion of the substrate.

2. The apparatus according to claim 1, further comprising:
    a first correction plate disposed between the first right-angled prism and the photographing part to reduce a path of light that has passed through the first right-angled prism; and
    a second correction plate disposed between the second right-angled prism and the photographing part to reduce a path of light that has passed through the second right-angled prism.

3. The apparatus according to claim 2, wherein the first correction plate and the second correction plate are formed of BK7.

4. The apparatus according to claim 1, wherein an angle between an upper surface and the inclined surface of the first right-angled prism and an angle between a lower surface and the inclined surface of the second right-angled prism are acute angles smaller than 45°.

5. The apparatus according to claim 1, further comprising a display part displaying the images taken by the photographing part.

6. The apparatus according to claim 1, further comprising an air nozzle for removing impurities from the edge portion of the substrate by ejecting air onto the edge portion of the substrate.

7. The apparatus according to claim 1, further comprising a transportation part transporting the substrate.

* * * * *